US008883413B2

(12) United States Patent
Lambris

(10) Patent No.: US 8,883,413 B2
(45) Date of Patent: *Nov. 11, 2014

(54) COMPSTATIN ANALOGS WITH IMPROVED ACTIVITY

(75) Inventor: John D. Lambris, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 176 days.

This patent is subject to a terminal disclaimer.

(21) Appl. No.: 13/177,140

(22) Filed: Jul. 6, 2011

(65) Prior Publication Data

US 2011/0275150 A1    Nov. 10, 2011

Related U.S. Application Data

(62) Division of application No. 10/528,496, filed as application No. PCT/US03/29653 on Sep. 22, 2003, now Pat. No. 7,989,589.

(60) Provisional application No. 60/412,220, filed on Sep. 20, 2002.

(51) Int. Cl.
| | |
|---|---|
| *C12Q 1/68* | (2006.01) |
| *A61K 38/10* | (2006.01) |
| *C07K 7/08* | (2006.01) |
| *C07K 14/47* | (2006.01) |

(52) U.S. Cl.
CPC . *C07K 7/08* (2013.01); *A61K 38/10* (2013.01); *C07K 14/472* (2013.01)
USPC .............................. 435/6.1; 530/327; 514/1.1

(58) Field of Classification Search
CPC ......... C12Q 1/68; A61K 38/10; C07K 14/472
See application file for complete search history.

(56) References Cited

U.S. PATENT DOCUMENTS

| | | | |
|---|---|---|---|
| 4,299,838 A | 11/1981 | Durlach | |
| 4,576,750 A | 3/1986 | Pitzenberger | |
| 4,807,097 A | 2/1989 | Gammache | |
| 5,167,960 A | 12/1992 | Ito et al. | |
| 5,256,642 A | 10/1993 | Fearon et al. | |
| 5,776,970 A | 7/1998 | Shechter et al. | |
| 6,169,057 B1 | 1/2001 | Lovatt | |
| 6,214,790 B1 | 4/2001 | Richelson et al. | |
| 6,319,897 B1 | 11/2001 | Lambris et al. | |
| 7,888,323 B2 * | 2/2011 | Lambris et al. | 514/20.6 |
| 7,989,589 B2 * | 8/2011 | Lambris | 530/327 |
| 2001/0023066 A1 | 9/2001 | Kinders et al. | |

FOREIGN PATENT DOCUMENTS

| | | |
|---|---|---|
| WO | WO 91/16345 A1 | 10/1991 |
| WO | WO 95/23512 | 8/1995 |
| WO | WO 99/13899 A1 | 3/1999 |

OTHER PUBLICATIONS

Babitzke, et al., "Structural Features of L-Tryptophan Required for Activation of Trap, the trp RNA-binding Attenuation Protein of . . . ", vol. 270 (21), pp, 12452-12456 (1995).

Beeley, N., "Pedidomimetrics and small-molecular drug design: towards improved bioavailability and in vivo stability", Trends Biotechnol., vol. 12, pp. 213-216 (1994).
Beene, et al., "Cation-π Interactions in Ligand Recognition by Serotonergic (5-HT3A) and Nicotinic Acetylcholine Receptors: . . . ", Biochemistry, vol. 41, pp. 10262-10269 (2002).
Bowie et al., "Deciphering the Message in Protein Sequences: Tolerance to Amino acid Substitutions", Science, vol. 247, pp. 1306-1310 (1990).
Dennis, M.S., et al., "Albumin binding as a general strategy for improving pharmacokinetics of proteins", J. Biol. Chem., vol. 277, pp. 35035-35043 (2002).
Fiane, et al,, "Prolongation of Ex Vivo-Perfused Pig Xenograft Survival by the Complement . . . ", Transplantation Proceedings, vol. 31, pp. 934-935 (1999).
Fiane, et al. "Compstatin, a peptide inhibitor of C3, prolongs survival of ex vivo perfused pig xenografts", Xenotransplantation, vol. 6, pp. 52-65 (1999).
Fiane, et al., "Modulation of Fluid-Phase Complement Activation Inhibits Hyperacute Rejection in a Porcine . . . ", Transplantation Proceedings, vol. 32, pp. 899-900 (2000).
Furlong, et al., "C3 activation is inhibited by analogs of compstatin but not by serine protease inhibitors or peptidyl . . . ", Immunopharmacology, vol. 48, pp. 199-212 (2000).
Hruby, V.J., "Conformational and topographical considerations in the design of biologically active peptides", Biopolymers, vol. 33, pp. 1073-1082 (1993).
Kalli, et al., "Therapeutic uses of recombinant complement protein inhibitors", Springer Seminars in Immunopathology, vol. 15, pp. 417-431 (1994).
Klepeis, et al., "Predicting Peptide Structures Using NMR Data and Deterministic Global Optimization", Journal of Computational Chemistry, vol. 20 (13), pp. 1354-1370 (1999).
Klepeis, et al., Integrated Computational Experimental Approach for Lead Optimization and Design of Compstatin Variants . . . , J. Am. Chem. Soc., vol. 125, pp. 8422-8442 (2003).
Kozlowski, A., et al., "Development of pegylated interferons for the treatment of chronic hepatitis", BioDrugs, vol. 15, pp. 419-429 (2001).
Mallik, et al., "Conformational Interconversion in Compstatin Probed With Molecular . . . ", PROTEINS: Structure, Function, and Genetics, vol. 52, pp. 130-141 (2003).
Morikis, et al., "Solution structure of Compstatin, a potent complement inhibitor", Protein Science, vol. 7, pp. 619-627 (1998).
Morikis, et al., "Design, Structure, Function and Application of Compstatin", Bioactive . . . , J. Matsoulcas and T. Mavromousta (Eds), IOS Press, pp. 235-246 (1999).
Morikis, et al., "The Structural Basis of Compstatin Activity Examined by Structure-Function . . . ",The Journal of Biological Chemistry, vol. 277 (17), pp. 14942-14953 (2002).
Morikis, et al., "Structural aspects and design of low-molecular-mass complement inhibitors", Biochemical Society Transactions, vol. 30(6), pp. 1026-1036 (2002).

(Continued)

*Primary Examiner* — Maury Audet
(74) *Attorney, Agent, or Firm* — Potter Anderson and Corroon, LLP

(57) ABSTRACT

Compounds comprising peptides and peptidomimetics capable of binding the C3 protein and inhibiting complement activation are disclosed. These compounds display improved complement activation-inhibitory activity as compared with currently available compounds. Isolated nucleic acid molecules encoding the peptides are also disclosed.

6 Claims, 4 Drawing Sheets

(56) References Cited

OTHER PUBLICATIONS

Nilsson, et al., "Compstatin Inhibits Complement and Cellular Activation in Whole Blood in Two Models of Extracorporeal . . . ", Blood, vol. 92 (5), vol. 1661-1667 (1998).

Zacharias, et al., "Cation-π interactions in ligand recognition and catalysis", Trends in Pharmacological Sciences 23 (6):281-287 (2002).

Zhao, B., et al., "A paradigm for drug discovery using a conformation from the crystal structure of a presentation scaffold", Nat. Struct. Biol., vol. 2, pp. 1131-1137 (1995).

Notice of Allowance issued on Mar. 22, 2011, in U.S. Appl. No. 10/528,496, filed Dec. 22, 2005.

Non-final Office Action issued on Jun. 22, 2010, in U.S. Appl. No. 10/528,496, filed Dec. 22, 2005.

Restriction Requirement issued on May 16, 2006, in U.S. Appl. No. 10/528,496, filed Dec. 22, 2005.

Notice of Allowance issued on Sep. 27, 2010, in U.S. Appl. No. 11/605,182, filed Nov. 28, 2006.

Final Office Action issued on Mar. 3, 2010, in U.S. Appl. No. 11/605,182, filed Nov. 28, 2006.

Non-Final Office Action issued on Jun. 30, 2009, in U.S. Appl. No. 11/605,182, filed Nov. 28, 2006.

Ngo, et al., "Computational Complexity, Protein Structure Prediction, and the Levinthal . . . ", The Protein Folding Problem and Tertiary Structure Prediction, pp. 492-495 (1994).

Sahu, et al., "Inhibition of Human Complement by a C3-Binding Peptide Isolated from a Phage-Displayed . . . ", Journal of Immunology, vol. 157, pp. 884-891 (1996).

Sahu, et al., Binding Kinetics, Structure-Activity Relationship, and Biotransformation of the Complement . . . , The Journal of Immunology, vol. 165, pp. 557-566 (2003).

Sahu, et al., "Compstatin, a peptide inhibitor of complement, exhibits species-specific binding to . . .", Molecular Immunology, vol. 39, pp. 557-566 (2003).

Schasteen, et al., "Synthetic Peptide Inhibitors of Complement Serine Proteases-III. Significant Increase . . . ", Molecular Immunology, vol. 28(1/2), pp. 17-26 (1991).

Soulika, et al., "Inhibition of Heparin/Protamine Complex-Induced Complement Activation by Cornpstatin in Baboons", Clinical Immunology, vol. 96 (3), pp. 212-221 (2000).

Soulika, et al., "Studies of Structure-Activity Relations Of Complement Inhibitor Compstatin", The Journal of Immunology, vol. 170, pp. 1881-1890 (2003).

Spruce, L., et al., "Chemical synthesis of small complement proteins and protein modules", International Immunopharmacology, vol. 2, pp. 1320-1321 (2002).

Veronese, F.M., "Peptide and protein PEGylation: a review of problems and solutions", Biomaterials, vol. 22, pp. 405-417 (2001).

Wang, Y., et al., "Amelioration of lupus-like autoimmune disease in NZBANF1 mice after treatment with a . . . ", Proc. Natl. Acad. Sci. USA, vol. 93, pp. 8563-8568 (1996).

* cited by examiner

SEQUENCE LISTING

```
<160> NUMBER OF SEQ ID NOS: 15

<210> SEQ ID NO 1
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: DISULFID
<222> LOCATION: (2)..(12)
<220> FEATURE:
<221> NAME/KEY: MOD_RES
<222> LOCATION: (13)..(13)
<223> OTHER INFORMATION: AMIDATION

<400> SEQUENCE: 1

Ile Cys Val Val Gln Asp Trp Gly His His Arg Cys Thr
1               5                   10

<210> SEQ ID NO 2
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<220> FEATURE:
```

```
<221> NAME/KEY: MOD_RES
<222> LOCATION: (13)..(13)
<223> OTHER INFORMATION: AMIDATION

<400> SEQUENCE: 2

Ile Cys Val Val Gln Asp Trp Gly His His Arg Cys Thr
1               5                   10

<210> SEQ ID NO 3
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (13)..(13)
<223> OTHER INFORMATION: AMIDATION

<400> SEQUENCE: 3

Ile Cys Val Tyr Gln Asp Trp Gly Ala His Arg Cys Thr
1               5                   10

<210> SEQ ID NO 4
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)

<400> SEQUENCE: 4

Ile Cys Val Trp Gln Asp Trp Gly Ala His Arg Cys Thr
1               5                   10

<210> SEQ ID NO 5
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (13)..(13)
<223> OTHER INFORMATION: AMIDATION

<400> SEQUENCE: 5

Ile Cys Val Trp Gln Asp Trp Gly Ala His Arg Cys Thr
1               5                   10

<210> SEQ ID NO 6
```

```
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (13)..(13)
<223> OTHER INFORMATION: D-threonine

<400> SEQUENCE: 6

Ile Cys Val Trp Gln Asp Trp Gly Ala His Arg Cys Thr
1               5                   10

<210> SEQ ID NO 7
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (4)..(4)
<223> OTHER INFORMATION: Xaa is 2-naphthylalanine
<220> FEATURE:
<221> NAME/KEY: MOD_RES
<222> LOCATION: (13)..(13)
<223> OTHER INFORMATION: AMIDATION

<400> SEQUENCE: 7

Ile Cys Val Xaa Gln Asp Trp Gly Ala His Arg Cys Thr
1               5                   10

<210> SEQ ID NO 8
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (4)..(4)
<223> OTHER INFORMATION: Xaa is 2-naphthylalanine

<400> SEQUENCE: 8

Ile Cys Val Xaa Gln Asp Trp Gly Ala His Arg Cys Thr
1               5                   10

<210> SEQ ID NO 9
<211> LENGTH: 13
<212> TYPE: PRT
<213> ORGANISM: Artificial sequence
```

```
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (4)..(4)
<223> OTHER INFORMATION: Xaa is 1-naphthylalanine

<400> SEQUENCE: 9

Ile Cys Val Xaa Gln Asp Trp Gly Ala His Arg Cys Thr
1               5                   10

<210> SEQ ID NO 10
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (4)..(4)
<223> OTHER INFORMATION: Xaa is 2 indanylglycine carboxylic acid
<220> FEATURE:
<221> NAME/KEY: MOD_RES
<222> LOCATION: (13)..(13)
<223> OTHER INFORMATION: AMIDATION

<400> SEQUENCE: 10

Ile Cys Val Xaa Gln Asp Trp Gly Ala His Arg Cys Thr
1               5                   10

<210> SEQ ID NO 11
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (4)..(4)
<223> OTHER INFORMATION: Xaa is 2 indanylglycine carboxylic acid

<400> SEQUENCE: 11

Ile Cys Val Xaa Gln Asp Trp Gly Ala His Arg Cys Thr
1               5                   10

<210> SEQ ID NO 12
<211> LENGTH: 13
<212> TYPE: PRT
<213> ORGANISM: Artificial sequence
<220> FEATURE:
<223> OTHER INFORMATION: synthetic sequence
<220> FEATURE:
```

<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (4)..(4)
<223> OTHER INFORMATION: Xaa is dihydrotryptophan

<400> SEQUENCE: 12

Ile Cys Val Xaa Gln Asp Trp Gly Ala His Arg Cys Thr
1               5                   10

<210> SEQ ID NO 13
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (2)..(12)
<220> FEATURE:
<221> NAME/KEY: MOD_RES
<222> LOCATION: (4)..(4)
<223> OTHER INFORMATION: Xaa is benzoylphenylalanine

<400> SEQUENCE: 13

Ile Cys Val Xaa Gln Asp Trp Gly Ala His Arg Cys Thr
1               5                   10

<210> SEQ ID NO 14
<211> LENGTH: 16
<212> TYPE: PRT
<213> ORGANISM: Artificial sequence
<220> FEATURE:
<223> OTHER INFORMATION: synthetic sequence
<220> FEATURE:
<221> NAME/KEY: DISULFID
<222> LOCATION: (3)..(13)

<400> SEQUENCE: 14

Gly Ile Cys Val Trp Gln Asp Trp Gly Ala His Arg Cys Thr Ala Asn
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: synthetic sequence
<220> FEATURE:
<221> NAME/KEY: MOD_RES
<222> LOCATION: (1)..(1)
<223> OTHER INFORMATION: Xaa is missing or is Gly
<220> FEATURE:
<221> NAME/KEY: MOD_RES
<222> LOCATION: (2)..(2)
<223> OTHER INFORMATION: Xaa is Ile, Val, Leu, Ac-Ile, Ac-Val, or Ac-Leu
<220> FEATURE:
<221> NAME/KEY: DISULFID
<222> LOCATION: (3)..(13)
<220> FEATURE:
<221> NAME/KEY: MOD_RES
<222> LOCATION: (5)..(5)
<223> OTHER INFORMATION: Xaa is Trp or a peptidic or non-peptidic analog
      of Trp

```
<220> FEATURE:
<221> NAME/KEY: MOD_RES
<222> LOCATION: (10)..(10)
<223> OTHER INFORMATION: Xaa is His, Ala, Phe or Trp
<220> FEATURE:
<221> NAME/KEY: MOD_RES
<222> LOCATION: (14)..(14)
<223> OTHER INFORMATION: Xaa is L-Thr, D-Thr, Ile, Val or Gly, any of
      which may be amidated
<220> FEATURE:
<221> NAME/KEY: MOD_RES
<222> LOCATION: (15)..(15)
<223> OTHER INFORMATION: Xaa is missing or is Ala
<220> FEATURE:
<221> NAME/KEY: MOD_RES
<222> LOCATION: (16)..(16)
<223> OTHER INFORMATION: Xaa is missing or is Asn, which may be amidated

<400> SEQUENCE: 15

Xaa Xaa Cys Val Xaa Gln Asp Trp Gly Xaa His Arg Cys Xaa Xaa Xaa
1               5                   10                  15
```

COMPSTATIN ANALOGS WITH IMPROVED ACTIVITY

Divisional of U.S. application Ser. No. 10/528,496, filed Dec. 22, 2005, which is a U.S. National Stage of PCT US/2003/029653, filed Sep. 22, 2003, which claims benefit of U.S. Application No. 60/412,220, filed Sep. 20, 2002, the entirety of each of which is incorporated by reference herein.

Pursuant to 35 U.S.C. §202(c), it is acknowledged that the United States Government may have rights in the invention described herein, which was made in part with funding from the National Institutes of Health, Grant Nos. AI 30040 and GM 62134.

FIELD OF THE INVENTION

This invention relates to activation of the complement cascade in the body. In particular, this invention provides peptides and peptidomimetics capable of binding the C3 protein and inhibiting complement activation.

BACKGROUND OF THE INVENTION

The complement system is the first line of immunological defense against foreign pathogens. Its activation through the classical, alternative or lectin pathways leads to the generation of anaphylatoxic peptides C3a and C5a and formation of the C5b-9 membrane attack complex. Complement component C3 plays a central role in activation of all three pathways. Activation of C3 by complement pathway C3 convertases and its subsequent attachment to target surface leads to assembly of the membrane attack complex and ultimately to damage or lysis of the target cells. C3 is unique in that it possesses a rich architecture that provides a multiplicity of diverse ligand binding sites that are important in immune surveillance and immune response pathways.

Inappropriate activation of complement may lead to host cell damage. Complement is implicated in several disease states, including various autoimmune diseases, and has been found to contribute to other clinical conditions such as adult respiratory syndrome, heart attack, rejection following xenotransplantation and burn injuries. Complement-mediated tissue injury has also been found to result from bioincompatibility situations such as those encountered in patients undergoing dialysis or cardiopulmonary bypass.

Complement-mediated tissue injuries are directly mediated by the membrane attack complex, and indirectly by the generation of C3a and C5a. These peptides induce damage through their effects on neutrophils and mast cells. In vivo, regulation of complement at the C3 and C5 activation steps is provided by both plasma and membrane proteins. The plasma protein inhibitors are factor H and C4-binding protein, and the regulatory membrane proteins located on cell surfaces are complement receptors 1 (CR1), decay-accelerating factor (DAF), and membrane cofactor protein (MCP). These proteins inhibit the C3 and C5 convertases (multi-subunit proteases), by promoting dissociation of the multisubunit complexes and/or by inactivating the complexes through proteolysis (catalyzed by factor I). Several pharmacological agents that regulate or modulate complement activity have been identified by in vitro assay, but most have been shown in vivo to be of low activity or toxic.

To date, there are no inhibitors of complement activation used in the clinic, though certain candidates for clinical use exist, specifically, a recombinant form of complement receptor 1 known as soluble complement receptor 1 (sCR1) and a humanized monoclonal anti-C5 antibody (5G1.1-scFv). Both of these substance's have been shown to suppress complement ctivation in in vivo animal models (Kalli et al., Springer Semin. Immunopathol. 15: 417-431, 1994; Wang et al., Proc. Natl. Acad. Sci. USA 93: 8563-8568, 1996). However, each substance possesses the disadvantage of being large molecular weight proteins (240 kDa and 26,000 kDa, respectively) that are difficult to manufacture and must be administered by infusion. Accordingly, recent research has emphasized the development of smaller active agents that are easier to deliver, more stable and less costly to manufacture.

U.S. Pat. No. 6,319,897 to Lambris et al. describes the use of a phage-displayed combinatorial random peptide library to identify a 27-residue peptide that binds to C3 and inhibits complement activation. This peptide was truncated to a 13-residue cyclic segment that maintained complete activity, which is referred to in the art as Compstatin. Compstatin inhibits the cleavage of C3 to C3a and C3b by C3 convertase. Compstatin has been tested in a series of in vitro, in vivo, ex vivo, and in vivo/ex vivo interface experiments, and has been demonstrated to: (1) inhibit complement activation in human serum (Sahu et al., J. Immunol. 157: 884-891, 1996); (2) inhibit heparin/protamine-induced complement activation in primates without significant side effects (Soulika et al., Clin. Immunol. 96: 212-221, 2000); (3) prolong the lifetime of a porcine-to-human xenograft perfused with human blood (Fiane et al., Transplant. Proc. 31: 934-935, 1999a; Fiane et al., Xenotransplantation 6: 52-65, 1999b; Fiane et al., Transplant. Proc. 32: 899-900, 2000); (4) inhibit complement activation in models of cardio-pulmonary bypass, plasmapheresis, and dialysis extra-corporeal circuits (Nilsson et al., Blood 92: 1661-1667, 1998); and (5) possess low toxicity (Furlong et al., Immunopharmacology 48: 199-212, 2000).

Compstatin is a peptide comprising the sequence ICVVQDWGHHRCT-$NH_2$ (SEQ ID NO:1), where Cys2 and Cys12 form a disulfide bridge. Its three-dimensional structure was determined using homonuclear 2D NMR spectroscopy in combination with two separate experimentally restrained computational methodologies. The first methodology involved distance geometry, molecular dynamics, and simulated annealing (Morikis et al., Protein Science 7: 619-627, 1998) and the second methodology involved global optimization (Klepeis et al., J. Computational Chemistry, 20: 1344-1370, 1999). The structure of Compstatin revealed a molecular surface that comprises of a polar patch and a non-polar patch. The polar part includes a Type I β-turn and the non-polar patch includes the disulfide bridge. In addition, a series of analogs with alanine replacements (an alanine scan) was synthesized and tested for activity, revealing that the four residues of the β-turn and the disulfide bridge with the surrounding hydrophobic cluster are essential for inhibitory activity (Morikis et al., 1998, supra).

Using a complement activity assay comprising measuring alternative pathway-mediated erythrocyte lysis, the $IC_{50}$ of Compstatin has been measured as 12 μM. Certain of the analogs previously tested have demonstrated activity equivalent to, or slightly greater than, Compstatin. The development of Compstatin analogs or mimetics with greater activity would constitute a significant advance in the art.

SUMMARY OF THE INVENTION

The present invention provides analogs and mimetics of the complement-inhibiting peptide, Compstatin (ICVVQDWGHHRCT-$NH_2$; SEQ ID NO:1), which have improved complement-inhibiting activity as compared to Compstatin.

In one aspect, the invention features a compound that inhibits complement activation, which comprises a peptide having a sequence:

(SEQ ID NO: 15)
Xaa1-Cys-Val-Xaa2-Gln-Asp-Trp-Gly-Xaa3-His-Arg-Cys-Xaa4;

wherein:
Xaa1 is Ile, Val, Leu, Ac-Ile, Ac-Val, Ac-Leu or a dipeptide comprising Gly-Ile;
Xaa2 is Trp or a peptidic or non-peptidic analog of Trp;
Xaa3 is His, Ala, Phe or Trp;
Xaa4 is L-Thr, D-Thr, Ile, Val, Gly, or a tripeptide comprising Thr-Ala-Asn, wherein a carboxy terminal —OH of any of the L-Thr, D-Thr, Ile, Val, Gly or Asn optionally is replaced by —NH$_2$; and the two Cys residues are joined by a disulfide bond.

In certain embodiments, Xaa1 is acetylated, and typically is Ac-Ile. In another embodiment, Xaa3 is Ala. In other embodiments, Xaa2 is an analog of Trp comprising a substituted or unsubstituted aromatic ring component, preferably comprising a bicyclic ring, (e.g., indole, naphthyl) or two rings (e.g., dibenzoyl). In exemplary embodiments, the analog of Trp is 2-naphthylalanine, 1-naphthylalanine, 2-indanylglycine carboxylic acid, dihydrotryptophan or benzoylphenylalanine.

In a particular embodiment, Xaa1 is Ac-Ile, Xaa2 is Trp or an analog of Trp comprising a substituted or unsubstituted indole, naphthyl or dibenzoyl component, Xaa3 is Ala and Xaa4 is L-threonine or D-threonine. Exemplary sequences are selected from the group consisting of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 and SEQ ID NO:13.

In another particular embodiment, Xaa1 is a dipeptide Gly-Ile, and Xaa 4 is a tripeptide Thr-Ala-Asn. An exemplary embodiment is a peptide having SEQ ID NO:14.

Another aspect of the invention features a compound that inhibits complement activation, comprising a non-peptide or partial peptide mimetic of the peptide described above, wherein one or more of the residues or analogs is replaced by a compound that enables retained or enhanced complement-activation inhibiting activity.

These compounds are of practical utility for any purpose for which Compstatin itself is utilized, as known in the art.

Another aspect of the invention features an isolated nucleic acid molecule encoding one or more peptides that inhibits complement activation, wherein the peptide comprises a sequence: Xaa1-Cys-Val-Xaa2-Gln-Asp-Trp-Gly-Xaa3-His-Arg-Cys-Xaa4 (SEQ ID NO:15);
wherein:
Xaa1 is Ile, Val, Leu, or a dipeptide comprising Gly-Ile;
Xaa2 is Trp;
Xaa3 is His, Ala, Phe or Trp; and
Xaa4 is L-Thr, D-Thr, Ile, Val, Gly, or a tripeptide comprising Thr-Ala-Asn; wherein the two Cys residues are joined by a disulfide bond.

The isolated nucleic acid molecule typically encodes a peptide wherein Xaa3 is Ala. In an exemplary embodiment, the isolated nucleic acid molecule encodes a peptide comprising SEQ ID NO:14. In another embodiment, the nucleic acid encodes a concatemer of two or more of a peptide comprising SEQ ID NO:14, wherein the encoded concatemer is cleavable by hydrazine to form a multiplicity of peptides comprising SEQ ID NO:14.

Expression vectors comprising any of the aforementioned isolated nucleic acid molecules are featured in another aspect of the invention, along with cells comprising the expression vectors, which may be bacterial, fungal, insect, plant or mammalian cells. Peptides encoded by these isolated nucleic acid molecules are useful for any purpose for which Compstatin is useful.

Various features and advantages of the present invention will be understood by reference to the detailed description, drawings and examples that follow.

DETAILED DESCRIPTION OF ILLUSTRATIVE EMBODIMENTS

Figure 1:
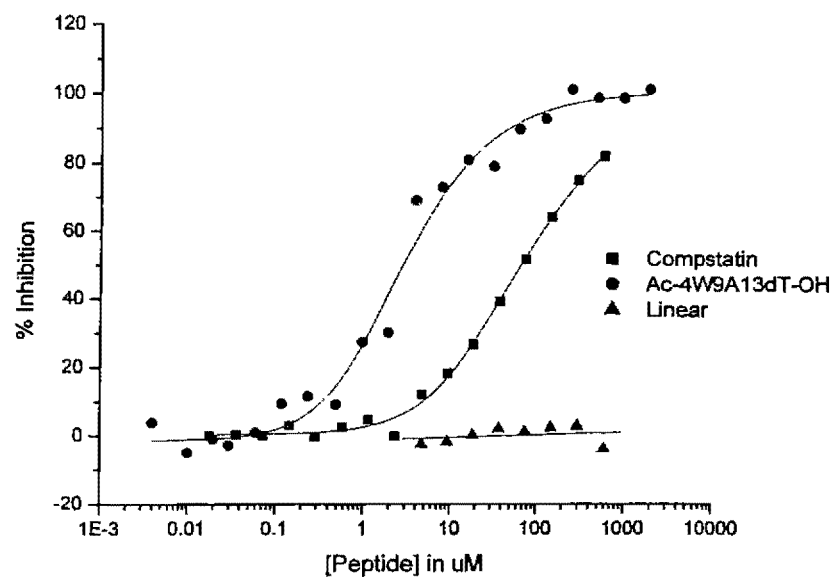
FIG. 1. Inhibition of complement activation by Compstatin (SEQ ID NO:1) and Ac-4W-9A-13dT-OH (SEQ ID NO:6). X axis is peptide concentration (µM), Y axis is inhibition of complement activation as measured by the assay described in Example 2; negative control is a linear peptide ("linear"), comprising Compstatin modified with alanine replacing cysteine at positions 2 and 12.
Figure 2:
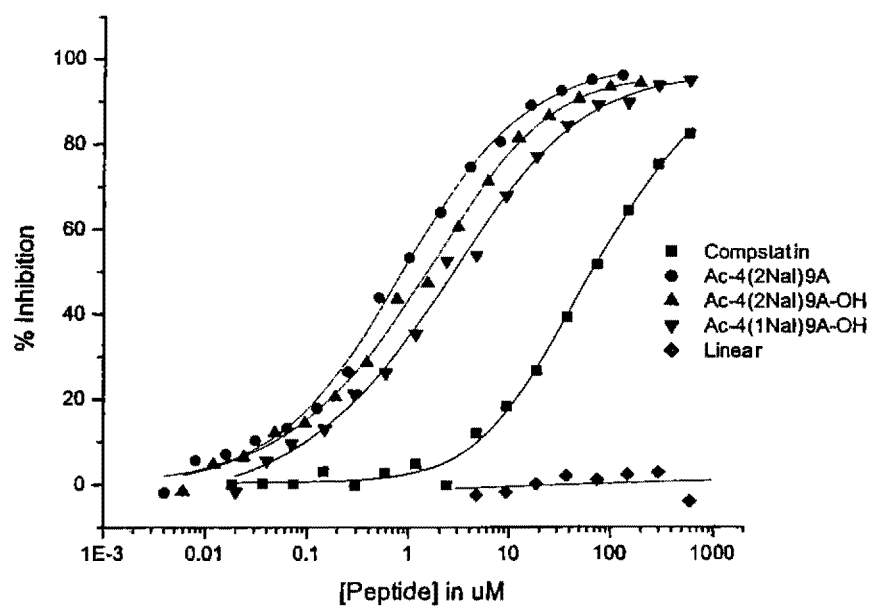
FIG. 2. Inhibition of complement activation by Compstatin (SEQ ID NO:1), Ac-4(2Nal)-9A (SEQ ID NO:7), Ac-4(2Nal)-9A-OH (SEQ ID NO:8) and Ac-4(1Nal)-9A-OH (SEQ ID NO:9). X axis is peptide concentration (µM), Y axis is inhibition of complement activation as measured by the assay described in Example 2; negative control is a linear peptide ("linear"), comprising Compstatin modified with alanine replacing cysteine at positions 2 and 12.
Figure 3:
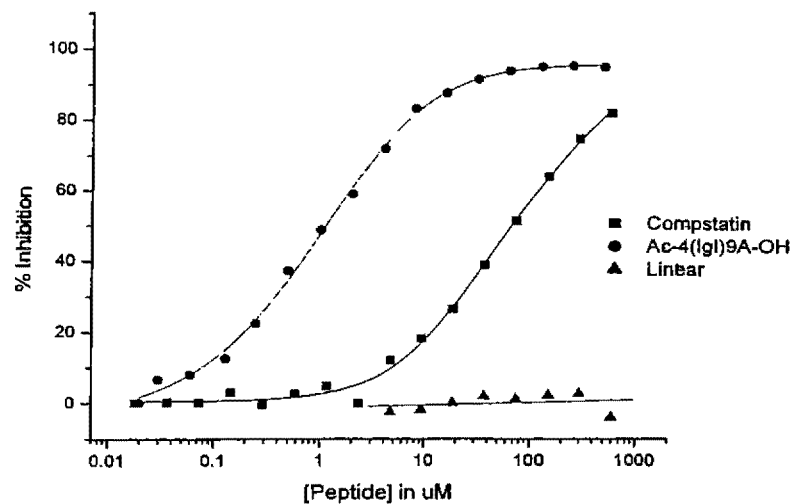
FIG. 3. Inhibition of complement activation by Compstatin (SEQ ID NO:1) and Ac-4(Ig1)-9A-OH (SEQ ID NO:11). X axis is peptide concentration (µM), Y axis is inhibition of complement activation as measured by the assay described in Example 2; negative control is a linear peptide ("linear"), comprising Compstatin modified with alanine replacing cysteine at positions 2 and 12.
Figure 4:
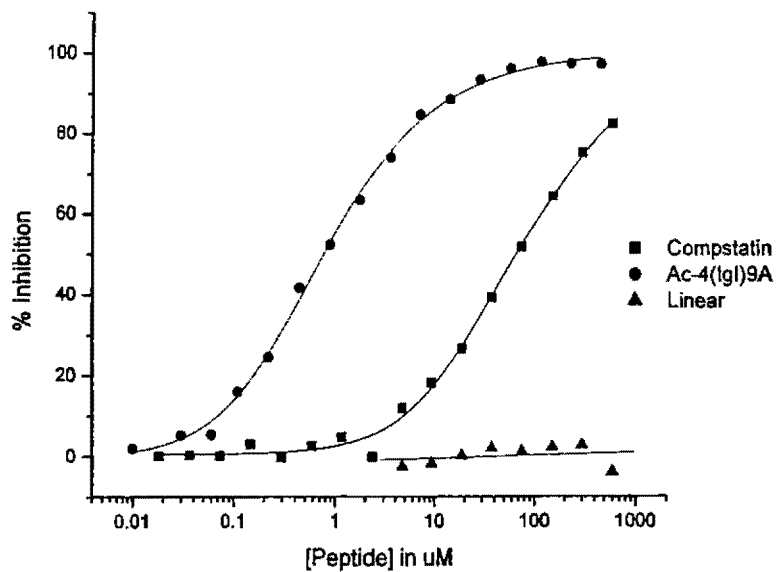
FIG. 4. Inhibition of complement activation by Compstatin (SEQ ID NO:1) and Ac-4(Ig1)-9A (SEQ ID NO:10). X axis is peptide concentration (µM), Y axis is inhibition of complement activation as measured by the assay described in Example 2; negative control is a linear peptide ("linear"), comprising Compstatin modified with alanine replacing cysteine at positions 2 and 12.
Figure 5:
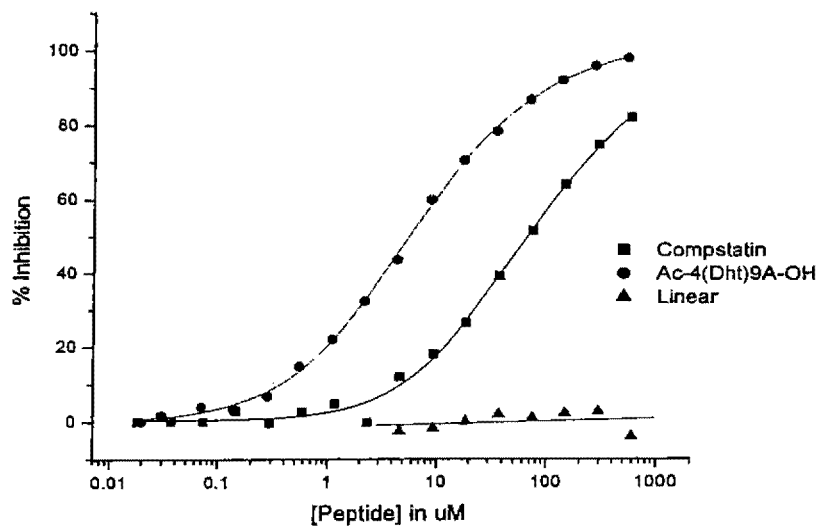
FIG. 5. Inhibition of complement activation by Compstatin (SEQ ID No:1) and Ac-4(Dht)-9A-OH (SEQ ID NO:12). X axis is peptide concentration (µM), Y axis is inhibition of complement activation as measured by the assay described in Example 2; negative control is a linear peptide ("linear"), comprising Compstatin modified with alanine replacing cysteine at positions 2 and 12.
Figure 6:
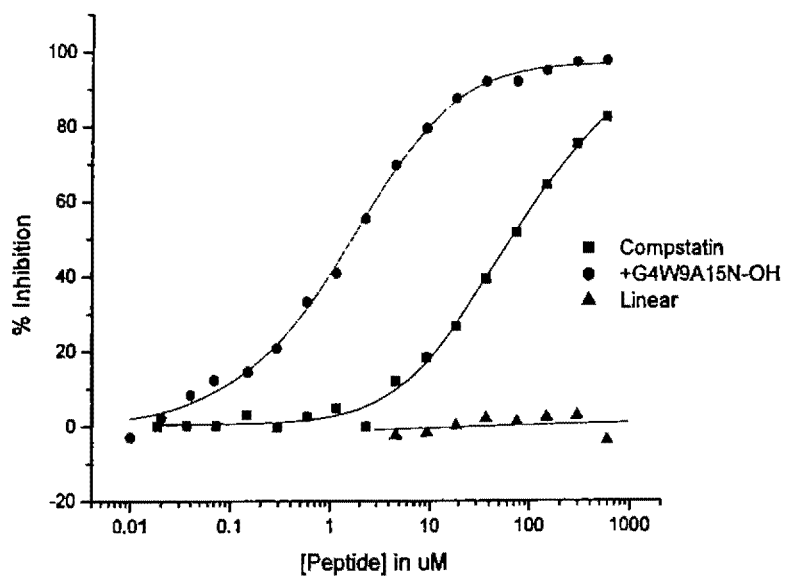
FIG. 6. Inhibition of complement activation by Compstatin (SEQ ID NO:1) and +G-4W-9A-15N-OH (SEQ ID NO:14). X axis is peptide concentration (µM), Y axis is inhibition of complement activation as measured by the assay described in Example 2; negative control is a linear peptide ("linear"), comprising Compstatin modified with alanine replacing cysteine at positions 2 and 12.
Figure 7:
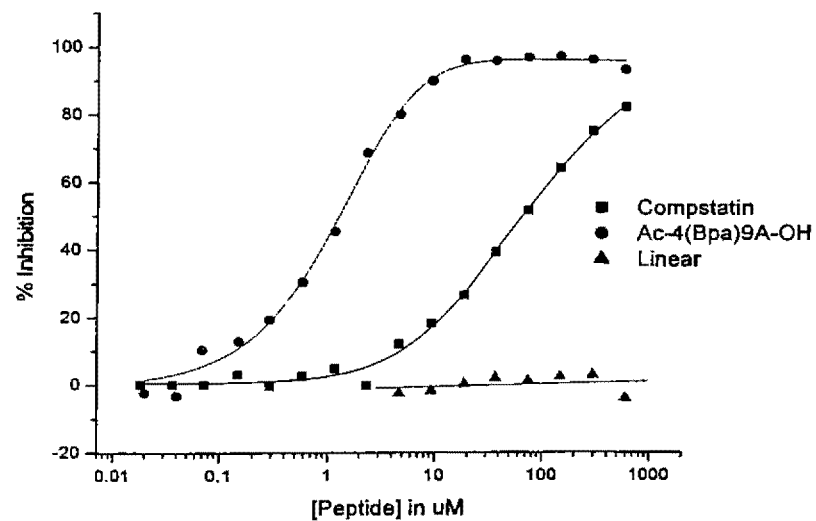
FIG. 7. Inhibition of complement activation by Compstatin (SEQ ID NO:1) and Ac-4(Bpa)-9A-OH (SEQ ID NO:13). X axis is peptide concentration (µM), Y axis is inhibition of complement activation as measured by the assay described in Example 2; negative control is a linear peptide ("linear"), comprising Compstatin modified with alanine replacing cysteine at positions 2 and 12.
Figure 8:
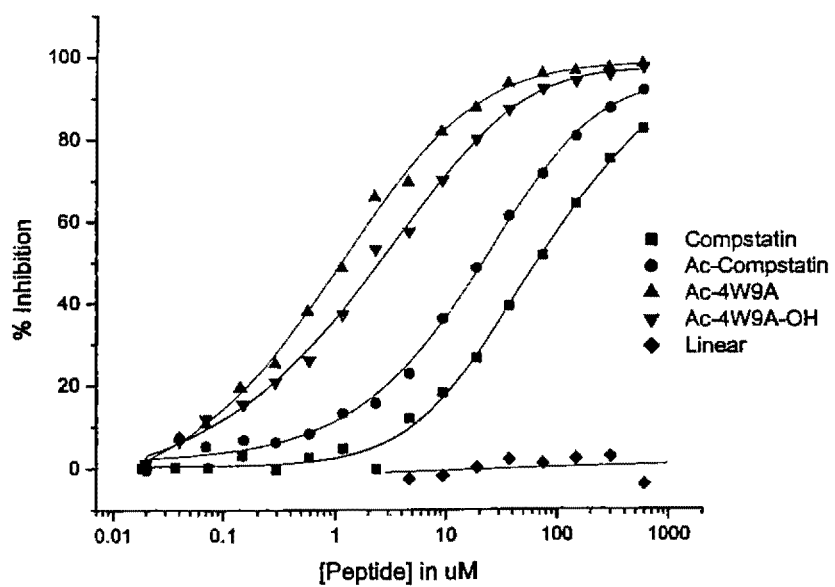
FIG. 8. Inhibition of complement activation by Compstatin (SEQ ID NO:1), Ac-Compstatin (SEQ ID NO:2), Ac-4W-9A (SEQ ID NO:5) and Ac-4W-9A-OH (SEQ ID NO:4). X axis is peptide concentration (µM), Y axis is inhibition of complement activation as measured by the assay described in Example 2; negative control is a linear peptide ("linear"), comprising Compstatin modified with alanine replacing cysteine at positions 2 and 12.

As employed above and throughout the disclosure, the following terms, unless otherwise indicated, shall be understood to have the following meanings.

The terms "pharmaceutically active" and "biologically active" refer to the ability of the compounds of the invention to bind C3 or fragments thereof and inhibit complement activation. This biological activity may be measured by one or more of several art-recognized assays, as described in greater detail herein.

As used herein, "alkyl" refers to a saturated straight, branched, or cyclic hydrocarbon having from about 1 to about 10 carbon atoms (and all combinations and subcombinations of ranges and specific numbers of carbon atoms therein), with from about 1 to about 7 carbon atoms being preferred. Alkyl groups include, but are not limited to, methyl, ethyl, n-propyl, isopropyl, n-butyl, isobutyl, t-butyl, n-pentyl, cyclopentyl, isopentyl, neopentyl, n-hexyl, isohexyl, cyclohexyl, cyclooctyl, adamantyl, 3-methylpentyl, 2,2-dimethylbutyl, and 2,3-dimethylbutyl.

As used herein, "halo" refers to F, Cl, Br or I.

As used herein, "aryl" refers to an optionally substituted, mono- or bicyclic aromatic ring system having from about 5 to about 14 carbon atoms (and all combinations and subcombinations of ranges and specific numbers of carbon atoms therein), with from about 6 to about 10 carbons being preferred. Non-limiting examples include, for example, phenyl and naphthyl.

As used herein, "aralkyl" refers to alkyl radicals bearing an aryl substituent and have from about 6 to about 20 carbon atoms (and all combinations and subcombinations of ranges and specific numbers of carbon atoms therein), with from about 6 to about 12 carbon atoms being preferred. Aralkyl groups can be optionally substituted. Non-limiting examples include, for example, benzyl, naphthylmethyl, diphenylmethyl, triphenylmethyl, phenylethyl, and diphenylethyl.

As used herein, the terms "alkoxy" and "alkoxyl" refer to an optionally substituted alkyl-O— group wherein alkyl is as previously defined. Exemplary alkoxy and alkoxyl groups include methoxy, ethoxy, n-propoxy, i-propoxy, n-butoxy, and heptoxy.

As used herein, "carboxy" refers to a —C(=O)OH group.

As used herein, "alkoxycarbonyl" refers to a —C(=O)O-alkyl group, where alkyl is as previously defined.

As used herein, "aroyl" refers to a —C(=O)-aryl group, wherein aryl is as previously defined. Exemplary aroyl groups include benzoyl and naphthoyl.

Typically, substituted chemical moieties include one or more substituents that replace hydrogen. Exemplary substituents include, for example, halo, alkyl, cycloalkyl, aralkyl, aryl, sulthydryl, hydroxyl (—OH), alkoxyl, cyano (—CN), carboxyl (—COOH), —C(=O)O-alkyl, aminocarbonyl (—C(=O)NH$_2$), —N-substituted aminocarbonyl (—C(=O)NHR"), CF$_3$, CF$_2$CF$_3$, and the like. In relation to the aforementioned substituents, each moiety R" can be, independently, any of H, alkyl, cycloalkyl, aryl, or aralkyl, for example.

As used herein, "L-amino acid" refers to any of the naturally occurring levorotatory alpha-amino acids normally present in proteins or the alkyl esters of those alpha-amino acids. The term D-amino acid" refers to dextrorotatory alpha-amino acids. Unless specified otherwise, all amino acids referred to herein are L-amino acids.

100421 In accordance with the present invention, information about the biological and physico-chemical characteristics of Compstatin have been employed to design Compstatin analogs with significantly improved activity compared to the parent Compstatin peptide. In preferred embodiments, the analogs have at least 5-fold greater activity than does Compstatin, preferably using the assay described in Example 2. More preferably, the analogs have 10-, 15-, 20-, 25-, 30-, 35-, 40-, 45-, or 50-fold greater activity, and even more preferably, 60-, 70- 80-fold or greater activity than does Compstatin, preferably utilizing the assay described in Example 2.

Compstatin analogs synthesized in accordance with other approaches have been shown to possess somewhat improved activity as compared with the parent peptide, i.e., up to six-fold (Klepeis, et al. 2003, JACS 125: 8422-8423). The analogs produced in accordance with the present invention possess even greater activity either the parent peptide or analogs thereof produced to date, as demonstrated by in vitro assays as shown in the figures and in Table 1 below.

Table 1 shows amino acid sequence and complement inhibitory activities of Compstatin and selected analogs with significantly improved activity. The selected analogs are referred to by specific modifications of designated positions (1-13) as compared to the parent peptide, Compstatin.

TABLE 1

| Peptide | Sequence | SEQ ID NO: | Activity over Compstatin |
|---|---|---|---|
| Compstatin | H-ICVVQDWGHHRCT-CONH2 | 1 | * |
| Ac-Compstatin | Ac-ICVVQDWGHHRGT-CONH2 | 2 | 3 × more |
| Ac-4Y,9A | Ac-ICVYQDWGAHRCT-CONH2 | 3 | 19 × more |
| Ac-4W,9A-OH | Ac-ICVWQDWGAHRCT-COOH | 4 | 25 × more |
| Ac-4W,9A | Ac-ICVWQDWGAHRCT-CONH2 | 5 | 55 × more |
| Ac-4W,9A13dT-OH | Ac-ICVWQDWGAHRCdT-COOH | 6 | 55 × more |
| Ac-4(2-Nal), 9A | Ac-ICV(2-Nal)QDWGAHRCT-CONH2 | 7 | 66 × more |
| Ac-4(2-Nal),9A-OH | Ac-ICV(2-Nal)QDWGAHRCT-COOH | 8 | 39 × more |

TABLE 1-continued

| Peptide | Sequence | SEQ ID NO: | Activity over Compstatin |
|---|---|---|---|
| Ac-4(1-Nal),9A-OH | Ac-ICV(1-Nal)QDWGAHRCT-COOH | 9 | 23 × more |
| Ac-4Igl,9A | Ac-ICVIglQDWGAHRCT-CONH2 | 10 | 55 × more |
| Ac-4Igl,9A-OH | Ac-ICVIglQDWGAHRCT-COOH | 11 | 55 × more |
| Ac-4Dht,9A-OH | Ac-ICVDhtQDWGAHRGT-COOH | 12 | 9 × more |
| Ac-4(Bpa),9A-OH | Ac-ICV(Bpa)QDWGAHRCT-COOH | 13 | 55 × more |
| +G,4W,9A +AN-OH | H-GICVWQDWGAHRCTAN-COOH | 14 | 38 × more | dT = D-threonine
2-Nal = 2-naphthylalanine
1-Nal = 1-naphthylalanine
Igl = 2 indanylglycine carboxylic acid
Dht = dihydrotryptophan
Bpa = benzoylphenylalanine Modifications at the N-terminus. Acetylation of the N-terminus typically increases the complement-inhibiting activity of Compstatin and its analogs, as can be seen specifically by comparing SEQ ID NO: 1 with SEQ ID NO:2. Accordingly, N-acetylation of the peptide is one preferred embodiment of the invention, of particular utility when the peptides are prepared synthetically. However, it is sometimes of advantage to prepare the peptides by expression of a peptide-encoding nucleic acid molecule in a prokaryotic or eukaryotic expression system, or by in vitro transcription and translation. For these embodiments, the naturally-occurring N-terminus is utilized. One example of a Compstatin analog suitable for expression in vitro or in vivo is that of SEQ ID NO:14, wherein the acetyl group is replaced by unmodified glycine at the N-terminus. SEQ ID NO:14, which additionally comprises Trp at position X4, Ala at position X9, and a C-terminal extension of Ala-Asn at positions X14 and X15, is 38-fold more active than Compstatin in the complement inhibition assay described herein.

Modification within the peptide. Using computational methods that the rank low lying energy sequences, it was previously determined that Tyr and Val were the most likely candidates at position 4 to support stability and activity of the peptide (Klepeis, et al., 2003, supra). In view of that determination, the present discovery that Trp at position 4, especially combined with Ala at position 9, yields many-fold greater activity than that of the parent peptide, is unexpected (for example, compare activities of SEQ ID NOS: 4, 5 and 6 with those of SEQ ID NOS: 2 and 3. Trp might be expected to contribute to the hydrophobic cluster involving residues at positions 1, 2, 3, 4, 12, and 13; however, its bulky side-chain mandates against the ability of a peptide comprising Trp to maintain its active conformation. Nonetheless, in accordance with the invention, Trp at position 4 of the peptide has been empirically determined to contribute significantly to the activity of the peptide.

Without intending to be limited by any particular mechanism of action, Trp at position 4 of the peptide may enhance activity by virtue of a cation-π interaction between the Trp aromatic side chain and cationic elements of the region of C3 with which the peptide interacts. It has been established that cation-π interaction, which is the electrostatic attraction between a cation and the negative electrostatic potential associated with the face of a simple π system, can contribute substantially to the binding of ligands to a broad range of protein classes (for a review, see Zacharias & Dougherty 2002, TIBS 23: 281-287).

Accordingly, modifications of Trp at position 4 (e.g., altering the structure of the side chain according to methods well known in the art), or substitutions of Trp analogs that maintain or enhance the aforementioned cation-π interaction, are contemplated in the present invention to produce analogs with even greater activity. For example, peptides comprising the tryptophan analogs 2-naphthylalanine (SEQ ID NOS: 7, 8), 1-naphthylalanine (SEQ ID NO: 9), 2-indanylglycine carboxylic acid (SEQ ID NOS: 10, 11) or dihydrotryptophan (SEQ ID NO: 12) at position 4 were all found to possess increased complement-inhibitory activity, ranging from 9-fold to 66-fold greater than Compstatin. In addition, a peptide comprising the phenylalanine analog, benzoylphenylalanine, at position 4 (SEQ ID NO: 13) possessed 55-fold greater activity that did Compstatin. It is believed that the planar two-ring compositions of these indole, naphthyl or dibenzoyl compounds enhances the π interaction afforded by the analog at position 4, thereby increasing the activity of the peptide. Accordingly, Trp analogs comprising two or more aromatic rings are preferred for use in the present invention. Such analogs are well known in the art and include, but are not limited to the analogs exemplified herein, as well as unsubstituted or alternatively substituted derivatives thereof. Examples of suitable analogs may be found by reference to the following publications, and many others: Beene, et al. (2002) Biochemistry 41: 10262-10269 (describing, inter alia, singly- and multiply-halogenated Trp analogs); Babitzke & Yanofsky (1995) J. Biol. Chem. 270: 12452-12456 (describing, inter alia, methylated and halogenated Trp and other Trp and indole analogs), and U.S. Pat. Nos. 6,214,790, 6,169,057, 5,776,970, 4,870,097, 4,576,750 and 4,299,838.

Modifications at the carboxy terminus. Peptides produced by synthetic methods are commonly modified at the carboxy terminus to comprise an amide instead of an acid; this common modification can be seen in Table 1 in Compstatin (SEQ ID NO:1) and several analogs. Indeed, in some instances, it has been determined that the terminal amide-containing peptides possess greater activity than do the terminal acid-containing peptides (compare, for example, SEQ ID NOS: 5 and 7 with SEQ ID NOS: 4 and 8, respectively). Accordingly, one preferred embodiment of the invention utilizes the C-terminal amide modification. However, some circumstances favor the use of a the acid at the C-terminus. Such circumstances include, but are not limited to solubility considerations and the expression of the peptides in vitro or in vivo from peptide-encoding nucleic acid molecules.

The carboxy-terminal residue of Compstatin is threonine. In some embodiments of the present invention, the C-terminal threonine is replaced by one or more naturally-occurring amino acids or analogs. For example, the peptide having SEQ ID NO:6 comprises D-threonine instead of L-threonine, and further possesses a COOH group at the C-terminus. This peptide shows activity equal to that of peptide SEQ ID NO:5, comprising L-threonine and $CONH_2$ at the C-terminus. Further, Ile has been substituted for Thr at position 13, to obtain a peptide with 21-fold greater activity than that of Compstatin. In addition, the peptide of SEQ ID NO:14, which comprises a C-terminal dipeptide extension of Ala-Asn, along with a COOH at the C-terminus and a non-acetylated N-terminus, demonstrates 38-fold greater activity than does Compstatin. It is also suitable for production via a prokaryotic or eukaryotic expression system, as described in greater detail below.

Another peptide that shows an increase in activity as compared with Compstatin comprises modifications in the N-terminal residue and within the peptide. This peptide comprises Ac-Leu at position 1, Trp at position 9 and Gly at position 13, but is unmodified at position 4.

The Compstatin analogs of the present invention may be prepared by various synthetic methods of peptide synthesis via condensation of one or more amino acid residues, in accordance with conventional peptide synthesis methods. Preferably, peptides are synthesized according to standard solid-phase methodologies, such as may be performed on an Applied Biosystems Model 431A peptide synthesizer (Applied Biosystems, Foster City, Calif.), according to manufacturer's instructions. Other methods of synthesizing peptides or peptidomimetics, either by solid phase methodologies or in liquid phase, are well known to those skilled in the art. During the course of peptide synthesis, branched chain amino and carboxyl groups may be protected/deprotected as needed, using commonly-known protecting groups. An example of a preferred peptide synthetic method is set forth in Example 1. Modification utilizing alternative protecting groups for peptides and peptide derivatives will be apparent to those of skill in the art.

Alternatively, certain peptides of the invention may be produced by expression in a suitable procaryotic or eucaryotic system. For example, a DNA construct may be inserted into a plasmid vector adapted for expression in a bacterial cell (such as *E. coli*) or a yeast cell (such as *Saccharomyces cerevisiae*), or into a baculovirus vector for expression in an insect cell or a viral vector for expression in a mammalian cell. Such vectors comprise the regulatory elements necessary for expression of the DNA in the host cell, positioned in such a manner as to permit expression of the DNA in the host cell. Such regulatory elements required for expression include promoter sequences, transcription initiation sequences and, optionally, enhancer sequences.

The peptide of SEQ ID NO:14, and others similarly designed, is particularly preferred for production by expression of a nucleic acid molecule in vitro or in vivo. A DNA construct encoding a concatemer of SEQ ID NO:14 (e.g., 2 or more of SEQ ID NO:14; the upper limit being dependent on the expression system utilized) may be introduced into an in vivo expression system. After the concatemer is produced, cleavage between the C-terminal Asn and the following N-terminal G is accomplished by exposure of the polypeptide to hydrazine.

The peptides produced by gene expression in a recombinant procaryotic or eucyarotic system may be purified according to methods known in the art. In a preferred embodiment, a commercially available expression/secretion system can be used, whereby the recombinant peptide is expressed and thereafter secreted from the host cell, to be easily purified from the surrounding medium.

The structure of Compstatin is known in the art, and the, structures of the foregoing analogs are determined by similar means. Once a particular desired conformation of a short peptide has been ascertained, methods for designing a peptide or peptidomimetic to fit that conformation are well known in the art. See, e.g., G. R. Marshall (1993), Tetrahedron, 49: 3547-3558; Hruby and Nikiforovich (1991), in Molecular Conformation and Biological Interactions, P. Balaram & S. Ramasehan, eds., Indian Acad. of Sci., Bangalore, PP. 429-455). Of particular relevance to the present invention, the design of peptide analogs may be further refined by considering the contribution of various side chains of amino acid residues, as discussed above (i.e., for the effect of functional groups or for steric considerations).

It will be appreciated by those of skill in the art that a peptide mimic may serve equally well as a peptide for the purpose of providing the specific backbone conformation and side chain functionalities required for binding to C3 and inhibiting complement activation. Accordingly, it is contemplated as being within the scope of the present invention to produce C3-binding, complement-inhibiting compounds through the use of either naturally-occurring amino acids, amino acid derivatives, analogs or non-amino acid molecules capable of being joined to form the appropriate backbone conformation. A non-peptide analog, or an analog comprising peptide and non-peptide components, is sometimes referred to herein as a "peptidomimetic" or "isosteric mimetic," to designate substitutions or derivations of the peptides of the invention, which possess the same backbone conformational features and/or other functionalities, so as to be sufficiently similar to the exemplified peptides to inhibit complement activation.

The use of peptidomimetics for the development of high-affinity peptide analogs is well known in the art (see, e.g., Zhao et al. (1995), Nature Structural Biology 2: 1131-1137; Beely, N. (1994), Trends in Biotechnology 12: 213-216; Hruby, V. J. (1993), Biopolymers 33: 1073-1082). Assuming rotational constraints similar to those of amino acid residues within a peptide, analogs comprising non-amino acid moieties may be analyzed, and their conformational motifs verified, by means of the Ramachandran plot (see Hruby & Nikiforovich, supra), among other known techniques.

The complement activation-inhibiting activity of Compstatin analogs and peptidomimetics may be tested by a variety of assays known in the art. In a preferred embodiment, the assay described in Example 2 is utilized. A non-exhaustive list of other assays is set forth in U.S. Pat. No. 6,319,897, including, but not limited to, (1) peptide binding to C3 and C3 fragments; (2) various hemolytic assays; (3) measurement of C3 convertase-mediated cleavage of C3; and (4) measurement of Factor B cleavage by Factor D.

The peptides and peptidomimetics described herein are of practical utility for any purpose for which Compstatin itself is utilized, as known in the art. Such uses include, but are not limited to: (1) inhibiting complement activation in the serum of a patient (human or animal); (2) inhibiting complement activation that occurs during use of artificial organs or implants (e.g., by coating or otherwise treating the artificial organ or implant with a peptide of the invention); (3) inhibiting complement activation that occurs during extracorporeal shunting of physiological fluids (blood, urine) (e.g., by coating the tubing through which the fluids are shunted with a peptide of the invention); and (4) in screening of small molecule libraries to identify other inhibitors of compstatin activation (e.g., liquid- or solid-phase high-throughput assays designed to measure the ability of a test compound to compete with a Compstatin analog for binding with C3 or a C3 fragment).

The following examples are provided to describe the invention in greater detail. They are intended to illustrate, not to limit, the invention.

EXAMPLE 1

Peptide Synthesis

Peptide synthesis and purification was performed as described by Sahu et al., 1996, supra, and Sahu et al., 2000, supra. Briefly, peptides were synthesized in an Applied Biosystem peptide synthesizer (model 431A) using Fmoc amide resin and standard side chain protecting groups. Peptides were cleaved from the resin by incubation for 3 hours at 22° C. with a solvent mixture containing 5% phenol, 5% thioanisole, 5% water, 2.5% ethanedithiol, and 82.5% trifluoroacetic acid (TFA). The reaction mixture was filtered through a fritted funnel, precipitated with cold ether, dissolved in 50% acetonitrile containing 0.1% TFA, and lyophilized. The crude peptides obtained after cleavage were dissolved in 10% acetonitrile containing 0.1% TFA and purified using a reverse phase C-18 column (Waters, Milford, Mass.). Disulfide oxidation was achieved by an on-resin cyclization method using the reagent Thallium (III) trifluoroacetate. This method eliminates the dilute solution oxidation steps and subsequent time-consuming concentration through lyophilization steps prior to reverse-phase HPLC. Using this method, the multimer formation was nonexistent and a high level (~90%) of fully deprotected, oxidized or cyclized material was obtained. The identity and purity of all peptides were confirmed by laser desorption mass spectroscopy and HPLC.

EXAMPLE 2

Complement Inhibition Assays

Inhibitory activity of Compstatin and its analogs on the complement system was determined by measuring their effect on the activation of the complement system by immunocomplexes. Complement activation inhibition was assessed by measuring the inhibition of C3 fixation to ovalbumin-anti-ovalbumin complexes in normal human plasma. Microtiter wells were coated with 50 µl of ovalbumin (10 mg/ml) for 2 hr at 25° C. (overnight at 4° C.). The wells were saturated with 200 µl of 10 mg/ml BSA for 1 hr at 25° C. and then a rabbit anti-ovalbumin antibody was added to form an immunocomplex by which complement can be activated. Thirty microliters of peptides at various concentrations were added directly to each well followed by 30 µl of a 1:80 dilution of human plasma. After 30 min incubation, bound C3b/iC3b was detected using a goat anti-human C3 HRP-conjugated antibody. Color was developed by adding ABTS peroxidase substrate and optical density measured at 405 nm. The concentration of the peptide causing 50% inhibition of C3b/iC3b deposition was taken as the $IC_{50}$ and used to compare the activities of various peptides.

All scientific articles, patents and other publications cited herein are incorporated by reference in their entireties. The present invention is not limited to the embodiments described and exemplified above, but is capable of variation and modification within the scope of the appended claims.

---

What is claimed:

1. An isolated nucleic acid molecule encoding one or more peptides that inhibits complement activation, wherein the peptide produced by expression of the nucleic acid molecule comprises amino acid sequence:

Xaa1-Cys-Val-Xaa2-Gln-Asp-Trp-Gly-Xaa3-His-Arg-Cys-Xaa4; (SEQ ID NO: 15)

wherein:

Xaa1 is Ile, Val, Leu, or a dipeptide comprising Gly-Ile;
Xaa2 is Trp;
Xaa3 is His, Ala, Phe or Trp; and
Xaa4 is L-Thr, D-Thr, Ile, Val, Gly, or a tripeptide comprising Thr-Ala-Asn;

wherein the two Cys residues are joined by a disulfide bond.

2. The isolated nucleic acid molecule of claim 1, encoding a peptide comprising the amino acid sequence of SEQ ID NO:15, wherein Xaa3 is Ala.

3. The isolated nucleic acid molecule of claim 2, encoding a peptide comprising the amino acid sequence of SEQ ID NO:14.

4. The isolated nucleic acid molecule of claim 3, encoding a concatemer of two or more of a peptide comprising the amino acid sequence of SEQ ID NO:14, wherein the encoded concatemer is cleavable by hydrazine to form a multiplicity of peptides comprising SEQ ID NO:14.

5. An expression vector comprising the isolated nucleic acid molecule of claim 1.

6. A bacterial, fungal, plant or insect cell comprising the expression vector of claim 5.

* * * * *